United States Patent [19]

Sridhar

[11] Patent Number: 5,463,121
[45] Date of Patent: Oct. 31, 1995

[54] PROCESS FOR THE REMOVAL OF WATER FROM ACRYLIC ACID

[75] Inventor: Srinivasan Sridhar, Marl, Germany

[73] Assignee: Huels Aktiengesellschaft, Marl, Germany

[21] Appl. No.: 319,017

[22] Filed: Oct. 6, 1994

[30] Foreign Application Priority Data

Jan. 19, 1994 [DE] Germany ............... 44 01 405.8

[51] Int. Cl.$^6$ ............................................. C07C 51/42
[52] U.S. Cl. ............................................... 562/600
[58] Field of Search ............................................... 562/600

[56] References Cited

U.S. PATENT DOCUMENTS

| 4,166,774 | 9/1979 | Wagner et al. .......... 562/600 |
|---|---|---|
| 4,755,299 | 7/1988 | Brueschke . |
| 4,915,834 | 4/1990 | Brueschke . |
| 4,978,430 | 12/1990 | Nakagawa et al. . |
| 5,156,740 | 10/1992 | Brueschke . |
| 5,296,144 | 3/1994 | Sternina et al. .......... 210/490 |

FOREIGN PATENT DOCUMENTS 0096339  12/1983  European Pat. Off. .

Primary Examiner—José G. Dees
Assistant Examiner—Dwayne C. Jones
Attorney, Agent, or Firm—Oblon, Spivak, McClelland, Maier & Neustadt

[57] ABSTRACT

The removal of water from aqueous acrylic acid solutions is carried out by removing 10 to 90 wt. % of the water by pervaporation. Subsequent work-up of the acrylic acid by distillation is thereby made easier.

15 Claims, 1 Drawing Sheet

PROCESS FOR THE REMOVAL OF WATER FROM ACRYLIC ACID

BACKGROUND OF THE INVENTION

1. Field of the Invention

The present invention relates to a new process for the removal of water from aqueous acrylic acid solutions.

2. Discussion of the Background

Acrylic acid can be prepared on a large industrial scale in various ways, the processes depending on the starting substance. According to U.S. Pat. No. 2,922,815, acrylic acid can be prepared from acetylene, carbon monoxide and water. In this process, the water remains as an excess in the product stream. Water is also used in the hydrolysis of acrylonitrile to acrylic acid according to U.S. Pat. No. 2,734,915. Excess water is consequently also obtained here, in addition to the product. Another possibility is, in accordance with U.S. Pat. No. 4,537,874, atmospheric oxidation of propylene to acrolein and subsequent further oxidation to acrylic acid. The reaction temperature is lowered drastically by supplying water (quenching), in order to end the reaction. Water is likewise obtained as a byproduct in this process. In the various processes, the product must subsequently be separated not only from the gaseous components which have not reacted but also from the water supplied or formed.

Various process variants have been proposed which realize removal of water from acrylic acid. If the water content is quite high, direct distillation of the water may prove to be uneconomical. Various processes are known for effecting the removal of water by an extraction step, extraction agents being, for example, ethyl acetate (GB 995 472), diisopropyl ether (GB 1 081 095), alkyl acrylates, ketones, β-alkyloxypropionate, derivatives of cyclohexanone (U.S. Pat. No. 3,657,332) or pyrrolidone. Acrylic acid is absorbed by the extraction agent and is recovered therefrom by distillation or by means of extractive distillation, crystallization or azeotropic distillation. When the water content is less than 60% in the starting mixture, the extraction step can be bypassed and water can be removed from the solution directly by azeotropic distillation. However, because of the exposure to heat, there is then also the risk of obstruction (clogging or blocking) due to polymerization, even if the acrylic acid is stabilized. Distillation at a low temperature under normal pressure would furthermore lead to high volumes of vapor and subsequently to large columns.

A preliminary process stage which reduces the water content in the solution significantly, for example to less than 40%, under mild conditions would be appropriate, so that the removal of water by distillation is limited to only a low water content. Pervaporation is a method in which a semipermeable membrane is introduced as a barrier for the organic substance in the transition from the liquid to the vapor phase. Since the membrane preferentially allows the passage of water, the separating action is promoted significantly. Numerous applications of pervaporation have been disclosed in recent years, for example for removal of water from organic solvents, alcohols and amines, a membrane which is essentially a separating layer of polyvinyl alcohol (PVA) allows selective removal of the water as a vapor phase.

According to Q. T. Nguyen (1991), Proc. Int. Conf,. Pervaporation Processes Chem. Ind. 5th, 67–78, customary PVA membranes are, however, unsuitable for pervaporation of aqueous acetic acid above 80° C., since the membrane in this case dissolves. The same also applies in particular to the even more aggressive aqueous mixture of acetic acid and chloroacetic acid. These strong organic acids can be concentrated only with the aid of special membranes. A special membrane of PVA, polyacrylate and polysulfone is accordingly used in U.S. Pat. No. 4,971,699 for pervaporation of aqueous formic or acetic acid. According to M. Yoshikawa (1993), J. Membrane Sci., 82, 157–62, aqueous acetic acid can also be pervaporated with the aid of a membrane of acrylic acid/acrylonitrile copolymers.

Pervaporation of aqueous acetic acid or an even stronger aqueous acid with the aid of PVA membranes is accordingly not recommended.

SUMMARY OF THE INVENTION

One object of the present invention is thus to concentrate aqueous acrylic acid solutions under mild conditions without an extraction agent and with a low expenditure of energy.

This object is achieved, surprisingly, by removing 10 to 90 wt. % of the water by pervaporation with the aid of a membrane.

DETAILED DESCRIPTION OF THE PREFERRED EMBODIMENTS

Figure 1:
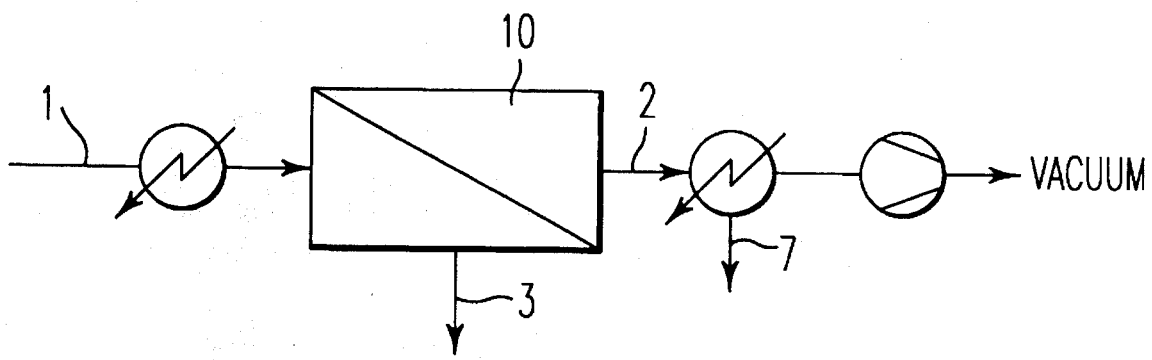
FIG. 1 shows a one-stage pervaporation embodiment of the present invention.

The process according to the invention can be carried out with the aid of a simple PVA membrane. This is surprising, because acrylic acid, with a pKa of 4.26, is an even stronger acid than acetic acid, with a pKa of 4.76, and should, therefore, be even more corrosive. One would expect, therefore, that removal of water from acrylic acid is not possible using a conventional PVA membrane at the required temperatures. The experience of the prior art suggests that the development of a membrane of other resistant materials would be necessary.

The pervaporation of the present method is preferably carried out at 60° to 100° C., temperatures of 70° to 95° C. being particularly preferred.

The pressure on the retained material side of the membrane is preferably 0.1 to 0.2 MPa, the process usually being carried out under normal pressure. The pressure on the permeate side, on the other side of the membrane, is preferably 1 to 900, in particular 70 to 200 hPa. A slight vacuum is thus preferably applied. In a specific embodiment, an inert gas, such as for example, nitrogen, is used under normal pressure or under a vacuum on the permeate side.

Suitable membranes comprise, for example, PVA, polyimide, polysulfone, polyphenylene oxide, polyvinyl carbonate (PVC) or vinyl alcohol/vinyl acetate, acrylic acid/acrylonitrile, vinylpyridine/acrylonitrile or vinyl acetate/vinylpyrrolidone copolymers. Membranes having a separating layer comprising PVA or PVA to the extent of more than 90 wt. % are preferably used because of a high permeability and selectivity coupled with adequate stability.

Twenty to 70 wt. % strength aqueous acrylic acid solutions are preferably employed for the pervaporation, the concentration being, more preferably, 40 to 60 wt. %. The concentrated solution (the retained material) is preferably 60 to 95 wt. % strength. Seventy to 80 wt. % strength acrylic acid solutions are particularly preferably prepared by the pervaporation. In the ideal case, the permeate is free from acrylic acid. In practice, the acrylic acid content in the permeate is preferably less than 20 wt. %, the concentrations particularly preferably being 1 to 10 wt. %.

The pervaporation can be carried out continuously or discontinuously. A one-stage or a multi-stage pervaporation, for example a cascade of pervaporation steps, can also be carried out. When removing water in a plurality of process stages, the acrylic acid in the permeate can be concentrated by pervaporation or also by reverse osmosis. In a preferred embodiment, in a multi-stage removal of water, pervaporation is carried out at least in the first stage and reverse osmosis is carried out at least in the last stage, and if appropriate also in the stages before, but not in the 1st stage. According to this specific procedure, for example in the case of removal of water in 4 process stages, reverse osmosis is thus carried out in the 4th and if appropriate also in the 2nd and 3rd stage.

A one-stage pervaporation is shown in FIG. 1. Starting acrylic acid-water mixture 1 is metered into pervaporation unit 10. Because of the trans-membrane gradient in water concentration, the water from the solution passes through the membrane of unit 10 into the permeate zone, while acrylic acid is held back by the membrane. The water-rich permeate is drawn off as stream 2, while the acid is chiefly obtained in the retained material stream 3. If a significant content of acrylic acid penetrates through the membrane, the pervaporation can also be carried out in several stages as a cascade, so that the permeate 7 from the last stage is free from acid (less than 1 wt. %). At the same time, the retained material from the first stage can thereby be enriched in acid.

Figure 2:
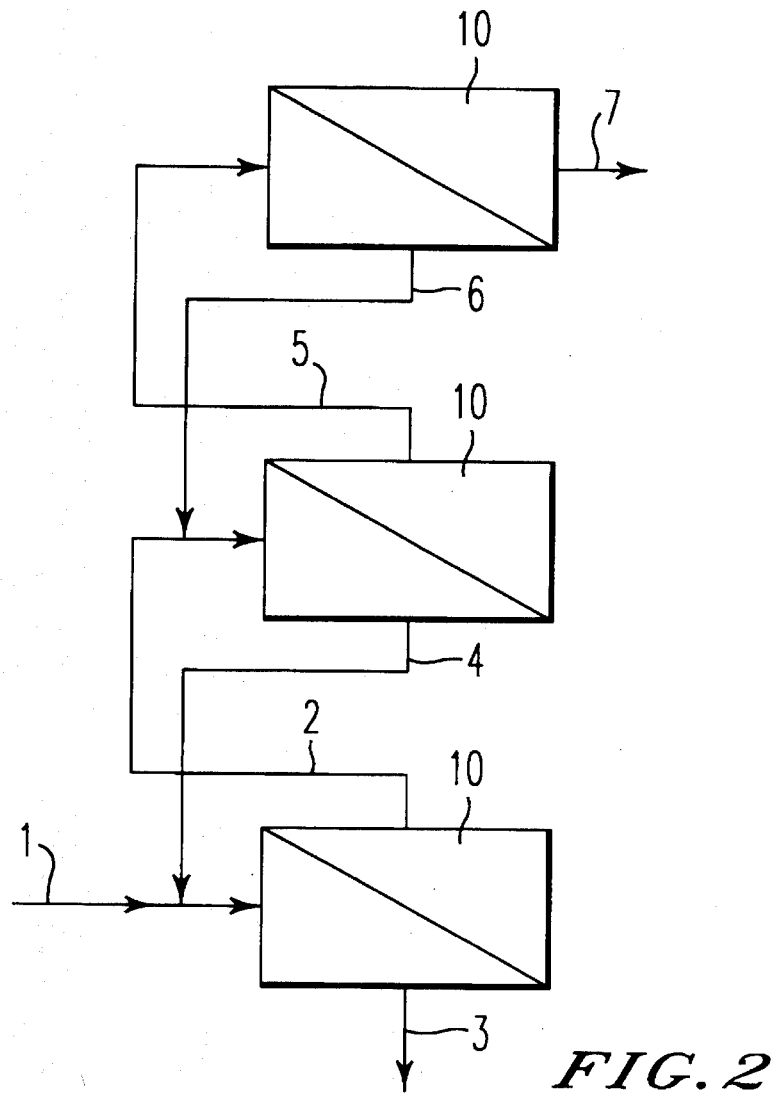
FIG. 2 shows a three-stage pervaporation cascade embodiment of the invention.

FIG. 2 shows a 3-stage cascade of three perevaporation units 10 in which, for example, retained material (stream 3) containing 30 wt. % of water and a final permeate (stream 7) containing less than 1 wt. % acid are obtained from a starting mixture (stream 1) containing 50 wt. % water. The permeate from the 1st stage (stream 2) is fed to a 2nd stage and the retained material from the 2nd stage (stream 4) is recycled to the 1st stage. A similar procedure is also followed between the 2nd and the 3rd stage. The final permeate appears from the 3rd stage. After each stage, the permeate can be either condensed or can remain in the vapor state. In the first case, the condensate is vaporized again before being fed to the next stage, and in the second case the vapor is compressed to normal pressure and introduced into the next stage in vapor form ("vapor permeation").

For economic reasons, it is often appropriate to operate the pervaporation only until the final permeate has an acid content of 1 to 5 wt. %, whereby further vaporization for the purpose of removal of the last residues of acid is avoided. Instead of further pervaporation, the final permeate is then subjected to reverse osmosis, which is carried out at normal temperature and without vaporization of the permeate. A permeate having an acid content of less than 1 wt. % can thereby be obtained, while the retained material of the reverse osmosis step, which is enriched in acid, is recycled to the pervaporation step.

The process according to the invention gives concentrated acrylic acid solutions under mild conditions with a low expenditure of energy. If pervaporation is used as an intermediate stage, the final distillation for complete removal of water is made significantly easier.

The following examples are intended to illustrate the invention. A one-stage pervaporation is carried out in Examples 1 to 7. In Examples 8 and 9, only the 3rd stage of a 3-stage cascade is considered.

EXAMPLES

Analytical methods used
  Water content: Karl-Fischer titration
  Acid content: Determination of acid number and gas chromatography (GC)

Example 1

20 cm$^2$ of a PVA membrane (Type 1005 from GFT, Deutsche Carbone GmbH, D-66540 Neunkirchen) was inserted in a pervaporation cell. Before the first use, the membrane was flushed in water for 40 hours. A starting mixture which contained acrylic acid, water and traces of acetic acid and was stabilized with hydroquinone was then allowed to flow over the membrane for 3 hours. The mixture was passed in circulation during this operation. The pressure on the permeate side was 5 hPa, the pressure on the retained material side was 0.1 MPa (normal pressure). In order to carry out the test under a constant feed composition, the permeate was drawn off continuously, condensed in a cold trap and recycled continuously to the starting mixture. After about 3 hours, the permeate was removed as a sample. The compositions of the starting mixture initially introduced and of the permeate sample are shown in Table 1, samples 1 to 8. The values show that the permeate has a considerably higher content of water than the starting mixture. Permeates containing less than 1 wt. % of acids are obtained from a high water content in the range of greater than 90 wt. % of water in the starting mixture.

Example 2

Pervaporation was carried out according to Example 1, but at a lower temperature of about 65° C. The pressure on the retained material side (operating pressure) was 0.12 MPa.

The results are shown in Table 1, samples 9 to 12.

Example 3

Pervaporation was carried out according to Example 1, but with a different PVA membrane (Type 1006 from GFT, Deutsche Carbone GmbH). The pressure on the permeate side was 5 hPa and the pressure on the retained material side was 0.12 MPa. The results are summarized in Table 1, samples 13 to 17.

Example 4

Pervaporation was carried out according to Example 1, but with the membrane of Example 3 and an increased pressure on the permeate side of 200 hPa and at 70° C. or 80° C. The results are shown in Table 1, samples 18 and 19.

Example 5

Pervaporation was carried out according to Example 1 with a starting mixture containing 91.7 wt. % water and 8.3 wt. % acrylic acid, but at an elevated temperature of 90° C. The acid content in the permeate was 1.0 wt. %. The permeate output corresponds to 3.55 kg/hour.m$^2$.

Example 6

Pervaporation was carried out according to Example 1, but with an increased pressure on the permeate side of 100 hPa. The starting mixture contained 35.5 wt. % water, 0.3 wt. % acetic acid and 64.2 wt. % acrylic acid. The permeate contained 69.3 wt. % water, 0.04 wt. % acetic acid and 30.7 wt. % acrylic acid. The permeate output corresponds to 2.3 kg/hour.m².

Example 7

Pervaporation was carried out according to Example 1, but under an increased pressure on the permeate side of 200 hPa. The starting mixture contained 35.8 wt. % water, 0.3 wt. % acetic acid and 63.9 wt. % acrylic acid. The water content in the permeate was 68.0 wt. %. The permeate output corresponds to 1.5 kg/hour.m².

Example 8

A starting mixture containing 1 wt. % acrylic acid and 99 wt. % water was subjected to reverse osmosis under 5 MPa at 35° C. 36 cm² of 3 different membranes (Type DESAL-DSG, DESAL-SE and DESAL-PS from DESALINATION, Escondido, Calif., U.S.A.) were employed. The permeate values for water at 35° C. under 5 MPa are:

DESAL-DSG 121.7 kg/hour.m²
DESAL-SE 63.3 kg/hour.m²
DESAL-PS 65.3 kg/hour.m²

The acid initially introduced was concentrated in this manner to an acid content (in the retained material) of 2.4 wt. %. The acid content in the permeate was usually 0.2 to 0.4 wt. %, and the flow rate was in the range from 16 to 40 kg/hour.m². The results are summarized in Table 2.

Example 9

A reverse osmosis was carried out according to Example 8, the concentration being carried out up to 6 wt. % acid in 38 hours. The acid content in the permeate was on average 0.2 to 0.9 wt. %, and the flow rate corresponded to 7 to 40 kg/hour.m². The results are shown in Table 3.

The temperatures for the pervaporation shown in the examples and the following tables relate to the feed. A temperature which is lower by about 5° C. in each case prevails at the membrane.

Obviously, numerous modifications and variations of the present invention are possible in light of the above teachings. It is therefore to be understood that within the scope of the appended claims, the invention may be practiced otherwise than as specifically described herein.

TABLE 1

| Sample | Starting mixture (% by weight) | | | Permeate (% by weight) | | | Permeate rate (kg/h · m²) | Temperature (°C.) | Duration of test (hours) |
|---|---|---|---|---|---|---|---|---|---|
| | Water | Acetic Acid | Acrylic acid | Water | Acetic acid | Acrylic Acid | | | |
| 1 | 11.2 | 0.3 | 88.6 | 63.9 | 0.2 | 35.9 | 1.05 | 70 | 2.5 |
| 2 | 28.9 | 0.3 | 70.8 | 74.4 | 0.1 | 25.5 | 2.15 | 72 | 3 |
| 3 | 37.8 | 0.8 | 61.4 | 80.3 | 0.3 | 19.4 | 2.04 | 73 | 2.67 |
| 4 | 51.4 | 1.5 | 47.1 | 88.0 | — | 11.6 | 2.45 | 70 | 2.2 |
| 5 | 59.3 | 1.3 | 39.4 | 91.6 | 0.3 | 8.1 | 2.48 | 70 | 2.5 |
| 6 | 68.3 | 1.1 | 30.6 | 93.8 | 0.2 | 6.0 | 3.00 | 74 | 2.5 |
| 7 | 83.6 | 0.5 | 15.9 | 97.6 | — | 2.4 | 2.11 | 74 | 2.5 |
| 8 | 96.4 | 0.1 | 3.8 | 100.0 | — | 0.15 | 1.49 | 74 | 2.5 |
| 9 | 10.3 | 0.4 | 89.4 | 60.2 | 0.2 | 39.6 | 0.85 | 65 | — |
| 10 | 29.3 | 0.8 | 68.8 | 77.7 | 0.3 | 22.0 | 1.49 | 65 | — |
| 11 | 41.1 | 1.2 | 57.7 | 83.2 | 0.4 | 16.5 | 1.95 | 67 | — |
| 12 | 58.1 | 1.5 | 40.3 | 91.3 | 0.3 | 8.4 | 2.20 | 67 | — |
| 13 | 30.6 | 1.6 | 67.8 | 48.2 | 0.9 | 50.3 | — | 73 | — |
| 14 | 40.7 | 1.4 | 57.9 | 59.6 | 1.0 | 37.4 | — | 74 | — |
| 15 | 46.5 | 1.8 | 51.6 | 66.3 | 1.2 | 32.8 | — | 70 | — |
| 16 | 49.5 | 3.2 | 47.2 | 66.8 | 1.7 | 31.4 | — | 75 | — |
| 17 | 69.7 | 1.1 | 29.2 | 79.8 | 0.7 | 19.5 | — | 75 | — |
| 18 | 90.9 | — | 9.1 | 87.3 | — | 6.6 | 4.19 | 80 | — |
| 19 | 93.4 | — | 6.1 | 94.9 | — | 5.1 | 2.38 | 70 | — |

TABLE 2

| Sample | Time (hr) | Retained material Acrylic acid (wt. %) | Permeate | | | | | |
|---|---|---|---|---|---|---|---|---|
| | | | DESAL-DSG | | DESAL-SE | | DESAL-PS | |
| | | | Acrylic acid (wt. %) | Permeate rate (kg/h · m²) | Acrylic acid (wt. %) | Permeate rate (kg/h · m²) | Acrylic acid (wt. %) | Permeate rate (kg/h · m²) |
| 1 | 0 | 1.0 | 0.32 | 39.7 | 0.2 | 22.9 | 0.17 | 25.7 |
| 2 | 2 | 1.2 | 0.38 | 36.5 | 0.25 | 21.1 | 0.25 | 28.3 |
| 3 | 5.5 | 2.4 | 0.54 | 27.7 | 0.36 | 16.4 | 0.32* | 17.9* |

*after 4 hours

TABLE 3

| | | Retained material Acrylic acid (wt. %) | Permeate | | | | | |
|---|---|---|---|---|---|---|---|---|
| | | | DESAL-DSG | | DESAL-SE | | DESAL-PS | |
| Sample | Time (hr) | | Acrylic acid (wt. %) | Permeate rate (kg/h · m²) | Acrylic acid (wt. %) | Permeate rate (kg/h · m²) | Acrylic acid (wt. %) | Permeate rate (kg/h · m²) |
| 1 | 0 | 1.05 | 0.28 | 39.9 | 0.18 | 26.0 | 0.15 | 30.3 |
| 2 | 2.17 | 1.22 | 0.35 | 35.9 | 0.21 | 22.8 | 0.21 | 26.9 |
| 3 | 8.50 | 1.70 | 0.45 | 31.6 | 0.26 | 19.9 | 0.28 | 23.8 |
| 4 | 15.42 | 1.96 | 0.51 | 28.6 | 0.30 | 17.5 | 0.28 | 21.6 |
| 5 | 22.33 | 2.31 | 0.55 | 27.6 | 0.32 | 16.8 | 0.31 | 20.8 |
| 6 | 29.25 | 3.04 | 0.73 | 22.8 | 0.41 | 13.3 | 0.41 | 16.6 |
| 7 | 36.25 | 4.56 | 1.27 | 16.5 | 0.72 | 8.7 | 0.68 | 11.1 |
| 8 | 38.75 | 6.02 | 1.62 | 14.6 | 0.93 | 7.1 | 0.82 | 9.4 |

What is claimed as new and desired to be secured by Letters Patent of the United States is:

1. A process for removing water from an aqueous acrylic acid solution, comprising:

removing 10 to 90 weight % of water from said solution by membrane pervaporation, wherein the membrane is formed of polyvinyl alcohol, polyimide, polysulfone, polyphenylene oxide, polyvinyl carbonate, vinyl alcohol/vinyl acetate copolymer, acrylic acid/acrylonitrile copolymer, vinylpyridine/acrylonitrile copolymer or vinyl acetate/vinylpyrrolidone copolymer.

2. The process of claim 1, wherein said pervaporation is carried out at 60° to 100° C.

3. The process of claim 2, wherein said pervaporation is carried out at 70° to 95° C.

4. The process of claim 1, wherein said pervaporation is carried out at a pressure of 0.1 to 0.2 MPa on the retained material side of said membrane and a pressure of 1 to 900 hPa, on the permeate side of said membrane.

5. The process of claim 4, wherein said pervaporation is carried out at normal pressure on the retained material side of said membrane and a pressure of 70 to 200 hPa on the permeate side of said membrane.

6. The process of claim 1, wherein an inert gas is fed to the permeate side of said membrane.

7. The process of claim 1, wherein said membrane has a separating layer consisting of polyvinyl alcohol or a separating layer comprising at least 90 wt. % polyvinyl alcohol.

8. The process of claim 1, wherein said acrylic acid solution is a 20 to 70 wt. % strength solution, retained material with a concentration of 60 to 95 wt. % strength is obtained and a permeate containing less than 20 wt. % acrylic acid is obtained.

9. The process of claim 8, wherein said acrylic acid solution is a 40 to 60 wt. % strength solution, retained material with a concentration of 70 to 80 wt. % strength is obtained and a permeate containing 1 to 10 wt. % acrylic acid is obtained.

10. The process of claim 1, wherein said process is a one stage process.

11. The process of claim 1, wherein said process has a plurality of stages.

12. The process of claim 11, wherein said pervaporation is carried out in at least the first stage of said plurality of stages.

13. The process of claim 11, further comprising removing water from a permeate using reverse osmosis in the last stage of said plurality of stages.

14. The process of claim 13, further comprising removing water from a permeate using reverse osmosis in the last stage and at least one other stage of said plurality of stages, with the proviso that said at least one other stage is not the first stage of said plurality of stages.

15. A process for removing water from an aqueous acrylic acid solution, comprising:

removing 10 to 90 weight % of water from said solution by membrane pervaporation, which utilizes a membrane of polyvinyl alcohol.

* * * * *